United States Patent
Stettler et al.

(10) Patent No.: US 9,783,770 B2
(45) Date of Patent: Oct. 10, 2017

(54) DEEPWELL PLATE SYSTEM WITH LID

(75) Inventors: Matt Stettler, LaCroix (GB); Adrian Haines, Shropshire (GB)

(73) Assignee: Lonza Biologics PLC, Slough (GB)

( * ) Notice: Subject to any disclaimer, the term of this patent is extended or adjusted under 35 U.S.C. 154(b) by 921 days.

(21) Appl. No.: 13/394,062

(22) PCT Filed: Aug. 14, 2010

(86) PCT No.: PCT/EP2010/005009
§ 371 (c)(1),
(2), (4) Date: Mar. 2, 2012

(87) PCT Pub. No.: WO2011/026559
PCT Pub. Date: Mar. 10, 2011

(65) Prior Publication Data
US 2012/0164725 A1 Jun. 28, 2012

(30) Foreign Application Priority Data
Sep. 5, 2009 (EP) .................................... 09011408

(51) Int. Cl.
| | | |
|---|---|---|
| C12M 1/00 | (2006.01) |
| B01L 3/00 | (2006.01) |
| C12M 1/32 | (2006.01) |
| C12M 3/00 | (2006.01) |
| C12N 5/071 | (2010.01) |

(52) U.S. Cl.
CPC ......... *C12M 23/38* (2013.01); *B01L 3/50853* (2013.01); *C12M 23/12* (2013.01); *B01L 2200/141* (2013.01); *B01L 2300/041* (2013.01); *B01L 2300/048* (2013.01)

(58) Field of Classification Search
CPC ........... B01L 3/50853; B01L 2200/141; B01L 2300/048; B01L 2300/041; C12M 23/38; C12M 23/12
USPC ....... 435/288.4, 305.3, 305.2; 422/400, 500; 356/246
See application file for complete search history.

(56) References Cited

U.S. PATENT DOCUMENTS

| | | | |
|---|---|---|---|
| 4,735,778 A | 4/1988 | Maruyama et al. | |
| 5,225,164 A * | 7/1993 | Astle | 422/553 |
| 5,417,923 A | 5/1995 | Bojanic et al. | |
| 2002/0006361 A1* | 1/2002 | Sanadi | 422/102 |

(Continued)

FOREIGN PATENT DOCUMENTS

| | | |
|---|---|---|
| DE | 102008008256 | 4/2009 |
| EP | 0866119 | 9/1998 |

(Continued)

OTHER PUBLICATIONS

International Search Report dated Nov. 3, 2010 in related International Application No. PCT/EP2010/005009.

(Continued)

*Primary Examiner* — Gautam Prakash
(74) *Attorney, Agent, or Firm* — Kilpatrick Townsend & Stockton LLP

(57) ABSTRACT

The present invention relates to a deepwell plate system, comprising a deepwell plate and a lid system which can be detachably fitted to the deepwell plate by snap- or clamp-fastening means so as to tightly seal the deepwell plate and to a method for the cultivation of cells within the deepwell plate system according to the present invention.

11 Claims, 8 Drawing Sheets

(56) References Cited

U.S. PATENT DOCUMENTS

| | | | |
|---|---|---|---|
| 2002/0176807 A1* | 11/2002 | Gubernator et al. | 422/102 |
| 2003/0108450 A1 | 6/2003 | Mainquist | |
| 2004/0089615 A1 | 5/2004 | Weiss | |
| 2005/0019224 A1* | 1/2005 | Pechter et al. | 422/102 |
| 2010/0248995 A1* | 9/2010 | Kensy et al. | 506/39 |

FOREIGN PATENT DOCUMENTS

| | | |
|---|---|---|
| EP | 1790414 | 5/2007 |
| EP | 1944080 | 7/2008 |
| JP | 2005527301 A | 9/2005 |
| WO | WO-9106368 | 5/1991 |
| WO | WO-9835013 | 8/1998 |
| WO | WO-2005118145 | 12/2005 |

OTHER PUBLICATIONS

International Preliminary Examination Report dated Dec. 9, 2011 in related International Application No. PCT/EP2010/005009.
Written Opinion of the International Preliminary Examining Authority dated Sep. 1, 2011 in related International Application No. PCT/EP2010/005009.

* cited by examiner

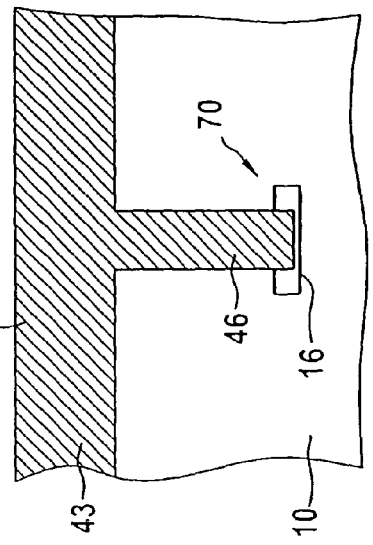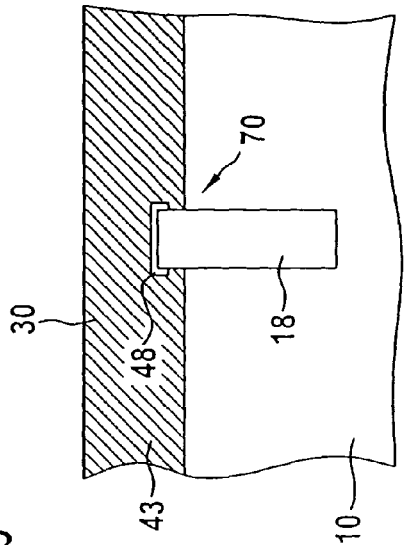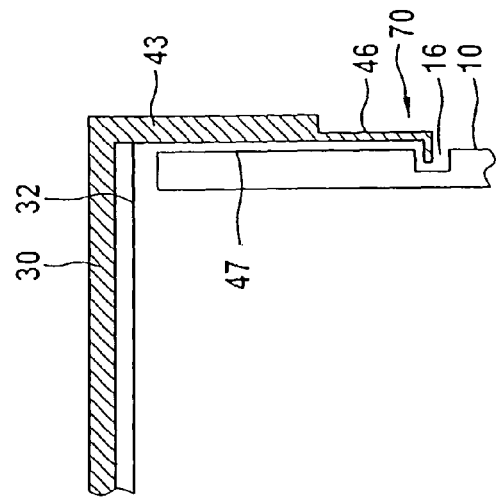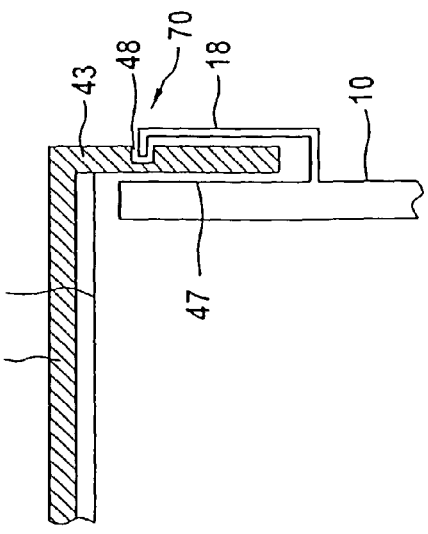
Fig. 4b
Fig. 5b
Fig. 4a
Fig. 5a

Fig. 6
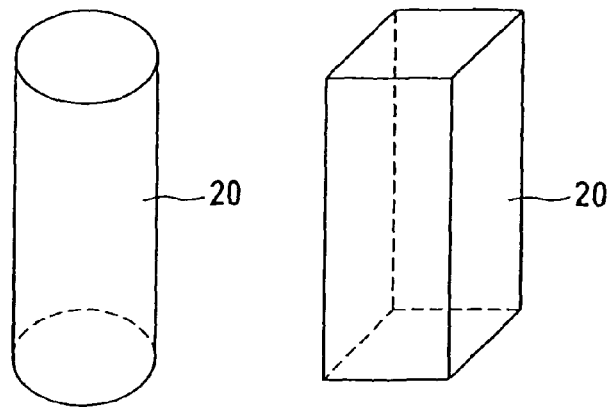
Fig. 7a  Fig. 7b
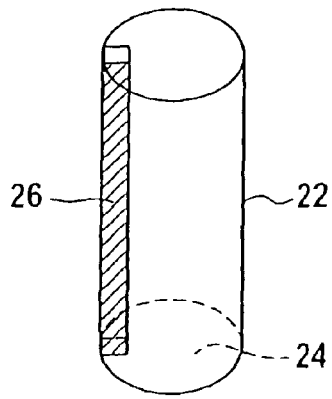 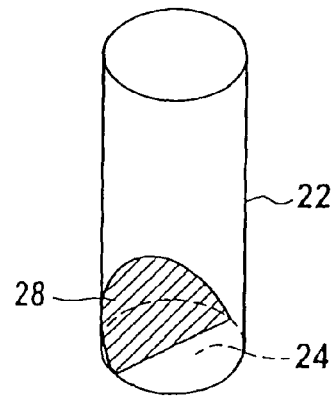
Fig. 7c
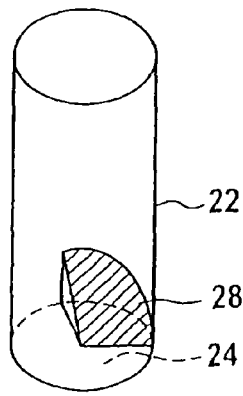

DEEPWELL PLATE SYSTEM WITH LID

CROSS REFERENCE TO RELATED APPLICATIONS

This application is the U.S. national phase of International Application No. PCT/EP2010/005009 filed on Aug. 14, 2010 as International Publication No. WO 2011/026559, which application claims priority to European Application No. 09011408.3 filed on Sep. 5, 2009, the contents of both of which are incorporated herein by reference in their entireties.

The present invention relates to a deepwell plate system, comprising a deepwell plate and a lid system which can be detachably fitted to the deepwell plate by lock elements, especially snap- or clamp-fastening means so as to tightly seal the deepwell plate and to a method for the cultivation of cells within the deepwell plate system according to the present invention.

So called multiwell or deepwell plates are commonly used in a variety of assays and methods using media or other test ingredients inoculated with cells or tissues to study cell growth, to carry out large scale protein, DNA or virus isolations or toxicity tests and the like. Such plates are disclosed for example in WO 05/118145, U.S. Pat. No. 4,735,778 and U.S. Pat. No. 5,417,923.

Multiwell plates comprise a plurality of cuvettes or wells to receive cell culture media or other liquid samples for the purpose of culturing cells, analyzing samples or storage of the same. As such multiwell or deepwell plates are often intended to be used with automated laboratory instrumentation, the Society for Biomolecular Screening (SBS) has published certain dimensional standards for these plates. This standardization has led to the manufacture of standardized plates as well as auxiliary equipment used for the handling of the plates which therefore are now usually compatible to each other. According to the SBS standards, industry standard multiwell plates are laid out with for example 96 wells in an 8×12 matrix having 8 rows of 12 wells. Also the height, length and width of the 96 well plates are standardized.

For cell-culture procedures it is often required that the cells or microorganisms are grown in a controlled atmosphere. Therefore, conventional standard multiwell plates have covers that fit only loosely onto the plates allowing gas exchange, reducing evaporation and minimizing cross contamination. To facilitate adequate oxygen transfer rates for cell or tissue culture within a multiwell plate, orbital shaking of the culture plate is often necessary. This in turn requires the closing of the culture plate in a leak-tight fashion to avoid any cross contamination between individual wells and excessive evaporation, but still allowing oxygen transfer.

Several leak-tight covering systems for multiwell plates are known in the art. There are for example special foils that can be sealed onto the plates using adhesives or heat. Furthermore, there are flexible mats which cover the wells with individual plug-like thicker parts which can be force-fit into the wells. Both of these methods cannot easily provide for both leak-tightness and sufficient oxygen transfer.

One example for the use of low- or deepwell multiwell plates in cell culture is the "system Duetz" from Enzy-Screen. In this system, cell culture is facilitated in well plates closed by a so called sandwich cover. Sandwich covers are clamped tightly onto the plates by externally provided clamps mounted onto the shaking device, thereby sandwiching the inner layers of the cover. The opening and closing of such a well plate cell culture is therefore a very laborious and time consuming process, which cannot be handled by automated laboratory equipment.

The technical problem underlying the present invention, thus, is to provide a deepwell plate with a lid that can be easily attached and detached to and from the plate, but still allows for sufficient oxygen transfer and is also compatible with standardized and automated laboratory equipment.

It is also a technical problem underlying the present invention to provide a deepwell plate system comprising a deepwell plate and a lid, covering said deepwell plate, which avoids the need of gluing the lid to the plate itself. It is furthermore a technical problem underlying the present invention to provide a deepwell plate system which is designed to reduce the risk of cross contamination between the individual wells. Yet another technical problem underlying the present invention is to provide a deepwell plate system which reduces the risk of contamination of the contents of the wells from the environment. It is also a technical problem underlying the present invention to provide a deepwell plate system which enables an improved efficiency of cultivation of microorganisms or cells by allowing for a larger volume of such cultures per individual well of the deepwell plate system and/or a reduced degree of orbital shaking.

The invention solves these problems by providing a deepwell plate system according to the main claim, particularly by the provision of a deepwell plate system, comprising a deepwell plate with a frame and 24 or 96 deepwells, wherein at least one well comprises at least one inner structure and a lid system. The lid system comprises at least one filter membrane and an outer cover, wherein the outer cover covers simultaneously all of the openings of the deepwells and includes at least one, preferably one, integrated lock element as a first locking portion and said first locking portion can be detachably fitted to at least one, preferably one, second locking portion located on the frame of the deepwell plate.

A further embodiment of the present invention is a deepwell plate system, comprising a deepwell plate with a frame and 24 or 96 deepwells and a lid system, wherein the lid system comprises at least one filter membrane and an outer cover, wherein the outer cover covers simultaneously all of the openings of the deepwells and includes at least one, preferably one, integrated lock element as a first locking portion and said first locking portion can be detachably fitted to at least one, preferably one, second locking portion located on the frame of the deepwell plate.

According to the present invention, the lid system, in particular the outer cover thereof, is stuck or clamped or otherwise secured to the deepwell plate with sufficient force to compress the at least one filter membrane and preferably the inner cover between the upper surface of the frame of the plate and the outer cover to seal, preferably hermetically seal the well openings. The deepwell plate system according to the present invention can then be placed in various orientations without loss of samples or contamination risk.

In the context of the present invention the term "deepwell plate system" is herein after sometimes called "a deepwell plate device" while the lid system is herein after sometimes called "the lid portion" and the "deepwell plate" is herein after sometimes called "the plate portion".

In connection with the present invention, the term "detachably fitted" is understood to mean that the lid system or the lid portion, of the deepwell plate system can easily be attached and detached to and from the plate portion in one piece in order to seal the complete plate in a liquid-tight fashion.

In connection with the present invention, the term "well" is understood to refer to the individual cuvettes or receptacles of the deepwell plate which can be in the form of a cupule, bore, hollowed out part or similar configuration and which are used for receiving samples, preferably liquid samples. One deepwell plate provides a plurality of such wells, preferably 24 or 96 wells. In a typical 96 well configuration each well can accommodate from 0.5 ml to 2.5 ml of a liquid sample.

The deepwell plate according to the invention comprises at least one frame which is preferably essentially in the form of a rectangle and comprises multiple wells or deepwells which are closed at the bottom and open towards the top. The wells or cuvettes that are formed in the frame part can have a circular, hexagonal, square or other geometric cross section.

The deepwell plate can be made of any suitable material, preferably plastic, for example polypropylene or polystryrene. The plastic or other suitable material may be colored according to the intended use or transparent to allow optical measurements.

According to the present invention the outer cover covers all the wells of the deepwell plate simultaneously in one single piece that means as a single unitary element. Preferably, the at least one filter membrane covers all the wells of the deepwell plate in one single piece, i.e. as a single unitary element. Preferably, the inner cover covers all the wells of the deepwell plate in one single piece, i.e. as one single unitary element. Hence, the top openings of the 24 or 96 wells are closed by at least one filter membrane and one outer cover, nevertheless sealing every individual well hermetically so as to avoid any cross contamination between the wells.

Thus, the deepwell plate device according to the invention comprises a frame and 24 or 96 deepwells formed within the frame part and a lid system covering all of the wells at once and thereby sealing each deepwell individually in a leak-tight fashion.

In connection with the present invention, the term "integrated lock element" is understood to refer to a locking means integrally provided with the outer cover of the lid system. The integrated lock element represents a first locking portion provided by the outer cover. Said first locking portion is intended to be engaged with a second locking portion provided on the frame of the deepwell plate. Preferably, the first locking portion is selected from the group consisting of protrusions, indentations, clamps and notches. In a preferred embodiment as a first locking portion the outer cover comprises solely protrusions. In a further preferred embodiment the first locking portion provided by the outer cover are indentations. In a further preferred embodiment of the present invention the first locking portion provided by the outer cover are clamps. In a furthermore preferred embodiment of the present invention the first locking portion provided by the outer cover are notches. However, in a furthermore, preferred embodiment it is also possible that more than one locking portion is provided by the outer cover, for instance two first locking portions, i.e. for instance protrusions and clamps. The second locking portion to which the first locking portion can be detachably fitted is a structural element being able and suitable to be detachably fitted to said first locking portion and thereby firmly holding the lid on the deepwell plate, in particular it is an element selected from the group consisting of protrusions, indentations, clamps and notches. In a particularly preferred embodiment the second locking portion is selected complementary to the first locking portion from the group consisting of protrusions, indentations, clamps and notches, for instance if the first locking portion is a protrusion, the second locking portion is an indentation or vice versa. It is also preferred that both the first and the second locking portion are protrusions.

In a preferred embodiment, the multiwell or deepwell plate according to the invention meets the published dimensional standards for multiwell plates of the Society for Biomolecular Screening (SBS), the so called ANSI-standards. One or more of the following ANSI-standards may be realized in the deepwell plate system according to the invention: ANSI/SBS 1-2004: Microplates-Footprint Dimensions; ANSI/SBS 2-2004: Microplates-Height Dimensions; ANSI/SBS 3-2004: Microplates-Bottom outside Flange Dimensions; ANSI-SBS 4-2004: Microplates-Well Positions. Providing a deepwell plate system according to the present invention that is in compliance with the SBS standards, thus makes the deepwell plate system compatible with automated laboratory equipment such as liquid handlers, stackers, grippers or barcode readers. Also, the deepwell plate system according to the present invention is thus stackable.

The deepwell plate as well as the lid system may be detoxified and/or sterilized by an appropriate means prior to use according to the requirements of the intended use. The surfaces of the deepwells may also be coated with special substances or materials according to the requirements of the intended use.

In a preferred embodiment, the lid system comprises an inner cover, at least one filter membrane and an outer cover.

The outer cover of the lid portion may be made of any suitable material, preferably resilient plastic, for example polypropylene or polystyrene.

In an advantageous embodiment, the outer cover of the lid system can be injection moulded in one piece.

The outer cover comprises preferably a number of small holes according to the number of wells of the plate used, preferably 24 or 96. In a preferred embodiment the holes are positioned according to the ANSI-standard defining the well positions so that each hole or opening comes to lie above the corresponding well to facilitate gas exchange. Thus, according to this embodiment the openings or small holes in the outer cover are in register or alignment with the openings of the wells such that access of gas, for instance oxygen, from the atmosphere to the well as well as an exchange of other gaseous substances is achievable through the filter membrane. In a preferred embodiment, the filter membrane located between the outer cover and the deepwell plate does not comprise such openings and therefore prevents any non-gaseous contamination from the atmosphere.

Thus, in a preferred embodiment the at least one filter membrane of the lid system according to the invention does not comprise any holes and may be gas-permeable and hydrophobic. Preferably the filter membrane is a microfiber filter, an PTFE filter or any other suitable filter membrane material. Preferably, the filter membrane is cut to fit into the outer cover and of an appropriate thickness and resilience, so that it can be compressed between the outer cover and the frame of the deepwell plate to seal the wells of the plate.

The inner cover of the lid system may preferably be made out of silicone or any other suitable material and is preferably pierced with small holes according to the number of wells of the plate used, preferably 24 or 96. In a preferred embodiment the holes are positioned according to the ANSI-standard defining the well positions so that each hole or opening comes to lie above the corresponding well to facilitate gas exchange. The inner cover is preferably cut to fit into the outer cover and of an appropriate thickness and resilience. In this particularly preferred embodiment, the inner cover and the filter membrane are sandwiched in a snug, liquid-tight fashion when the outer cover is attached to the deepwell plate.

In another preferred embodiment, the invention provides a deepwell plate system, wherein the first locking portion of the outer cover is a snap-fastening means. In a particularly preferred embodiment, the snap-fastening means of the deepwell plate system comprises at least two protrusions or a circumferential protrusion as the first locking portion extending inwardly of the plate matching lower portion of the rim of the outer cover to snap over at least two protrusions or a circumferential protrusion provided as the second locking portion extending outwardly of the lid matching upper portion of the deepwell plate.

In the context of the present invention, the term "inwardly" is understood to refer to the direction pointing towards the centre of the lid system or the plate portion of the deepwell plate system.

In connection with the present invention, the term "outwardly" is understood to refer to the direction pointing away from the centre of the lid system or the deepwell plate of the deepwell plate system.

The plate-matching lower portion of the rim of the outer cover and the lid-matching upper portion of the deepwell plate refer to those portions of the lid system and the deepwell plate, respectively, that overlap with each other while the lid is attached to the deepwell plate.

In the context of the present invention the term "protrusion" is understood to refer to a bulge-like extension provided at the plate-matching lower portion of the rim of the outer cover or the lid-matching upper portion of the deepwell plate.

In another particularly preferred embodiment of the invention, the snap-fastening means of the deepwell plate system comprises at least two indentations or a circumferential indentation as the first locking portion extending outwardly of the plate-matching lower portion of the rim of the outer cover to be engaged with at least two complementary protrusions or a complementary circumferential protrusion as the second locking portion extending outwardly of the lid-matching upper portion of the deepwell plate.

In the context of the present invention the term "indentation" refers to a groove formed within the plate-matching lower portion of the rim of the outer cover or the lid-matching upper portion of the deepwell plate.

In another preferred embodiment the snap-fastening means of the deepwell plate system comprises at least two protrusions or a circumferential protrusion as the first locking portion extending inwardly of the plate-matching lower portion of the rim of the outer cover to be engaged with at least two complementary indentations or a complementary circumferential indentation provided as the second locking portion extending inwardly of the lid-matching upper portion of the deepwell plate.

To close the lid by the snap-fastening means, it is thus only necessary to push the lid downwards onto the deepwell plate until the first and second locking portions engage by snapping or clicking over or into each other. For the purpose of opening the lid, only a small amount of force is needed to disengage the first and second locking portions as at least one of them is preferably made of resilient plastic.

Preferably, the engagement of the first locking portion and the second locking portion of the snap-fastening means, sandwiches the at least one filter membrane or the at least one filter membrane and the inner cover between the outer cover and the upper surface of the frame of the deepwell plate. Thereby, a liquid-tight sealing of the wells is achieved and, as the small holes of the outer cover or the outer cover and the inner cover are located above the center of each well, gas exchange is facilitated between the outside air and the inside of the well through the at least one filter membrane.

In another preferred embodiment, the lid-matching upper portion of the frame of the deepwell plate and the plate-matching lower portion of the rim of the outer cover are of such a height that it is possible to place the lid-system only loosely, but still securely, onto the plate without engaging the snap-fastening means.

In another alternative embodiment of the invention, the first locking portion of the outer cover is a clamp-fastening means. In one exemplary aspect, the clamp-fastening means of the deepwell plate system comprises at least two clamps, integrally fixed to the outer cover, as the first locking portion reaching to the side wall of the frame of the deepwell plate to be engaged with at least two complementary catch notches as the second locking portion located in the side wall of the frame of the deepwell plate.

In a preferred embodiment, the clamps or clips formed by the outer cover may have hook-shaped ends which can simply snap into the catch notches of the side wall of the frame of the deepwell plate. To close the lid, it is thus only necessary to push the lid downwards onto the plate until the fastening clamps or clips engage with the catch notches or apertures. For the purpose of opening the lid, the fastening clamps can be pulled away from the plate, so that they disengage from the catch notches.

In an alternative advantageous embodiment, the clamp-fastening means of the deepwell plate system comprises at least two catch notches as the first locking portion integrated in the outside rim of the outer cover to be engaged with at least two complementary clamps as the second locking portion located at the side wall of the frame of the deepwell plate reaching to the rim of the outer cover.

Preferably, the at least two clamps as well as the complementary catch notches are located on opposite sides of the deepwell plate and the lid system.

In an advantageous embodiment, the fastening clamps or clips do not alter the outside dimensions of the deepwell plate system so that it is still compliant with the ANSI-Standards and compatible to automated laboratory equipment.

In a particularly preferred embodiment of the invention, at least one well of the deepwell plate comprises at least one inner structure. The inner structure of the wells of the deepwell plate according to the invention can be symmetric or asymmetric. Said inner structure can be a projection or an elevation of the wall of the well. In a particularly preferred embodiment, the at least one inner structure of the wall of the well is a vertical mixing baffle.

In a preferred embodiment of the present invention the vertical mixing baffle is edged or round. In a particularly preferred embodiment a well comprises more than one, preferably four or six vertical mixing baffles, which can be edged or round. The size of such mixing baffles can of course be adjusted according to the intended use.

Thus, in a preferred embodiment of the present invention there is provided the advantageous teaching that due to the inner structures present in the wells, an improved supply, in particular of oxygen to the cultivated cells, is provided, which in turn allows a more efficient cultivation of cells, in particular allows to cultivate an increased number of microorganisms or cells in the specified volume. Furthermore, the improved cultivation facilitated by the present invention provides the further advantage that a reduced degree of mechanical agitation is necessary to achieve the intended oxygen transfer rates.

According to the present invention, the wells or cuvettes of the deepwell plate can have a circular, hexagonal, square or other geometric cross section. The bottom or base of each well can be flat, U-shaped, V-shaped, in form of a frustum or any other suitable shape.

In a preferred embodiment of the present invention the cross sections of the individual wells are flower-shaped, in particular in the shape of a four-edged flower, five-edged flower or six-edged flower.

In a preferred embodiment of the present invention the wells of the deepwell plate have star-shaped cross sections, in particular are five-edged or six-edged star-shaped.

Inner structures of the wall or the different geometries of the cross sections of the wells, for example in the form of vertical mixing baffles, flower- or star-shaped cross sections, allow in an advantageous manner improved agitation of the contents of the wells. Therefore, oxygen transfer is promoted which might allow for a reduced orbital shaking speed and/or increased working volume of the cell culture in each well. In a preferred embodiment, the vertical mixing baffle may be in the form of a straight fin, or may have a triangular or other shape.

The inner structure of the well of the deepwell plate system according to the invention can also be a projection or an elevation of the bottom of the well. Said projection or elevation of the bottom of the well can be a symmetric or asymmetric slope. Such a sloped or inclined base of the well assists in moving solid materials, or for example suspended cells, from the lower part of the well when the contents of the well are agitated and also provides for increased turbulence of the contents of the wells which in turn leads to increased oxygen transfer.

In a preferred embodiment of the deepwell plate system, the horizontal cross section of at least one well of the deepwell plate is asymmetric.

In a particularly advantageous embodiment, the deepwell plate, including the second locking portion and the possibly formed inner structures of the wells, may be injection moulded in one piece. In another advantageous embodiment, the outer cover of the lid system, including the first locking portion, may be injection moulded in one piece.

In a particularly preferred embodiment, the lid system according to the invention is integrally composed of the outer cover and the at least one filter membrane.

In another particularly preferred embodiment, the lid system is integrally composed of the outer cover, the at least one filter membrane and the inner cover.

The invention also provides a method for the cultivation of cells, preferably mammalian cells, wherein the cells are cultured in the deepwell plate system according to the invention. Therefore, individual wells are filled to a certain extend with any appropriate cell culture medium inoculated with cells, preferably mammalian cells, the lid system covers the wells in a liquid-tight fashion and agitation of the culture medium and oxygen transfer are provided by orbital shaking.

Further preferred embodiments of the present invention are the subject-matter of the subclaims.

The invention is further explained with reference to the accompanying drawing figures, provided for purposes of illustration only and not intended to define the scope of the present invention.

FIG. 4a shows a fragmentary cross-sectional view of one embodiment of the lock element as a clamp-fastening means.

FIG. 4b shows a plan view of the deepwell plate system with the clamp-fastening means described in detail with reference to FIG. 4a.

FIG. 5a shows a fragmentary cross-sectional view of another embodiment of the lock element as a clamp-fastening means.

FIG. 5b is a plan view of the deepwell plate system with the clamp-fastening means described in detail with reference to FIG. 5a.

FIG. 6 shows perspective views of individual wells.

FIG. 7a shows a perspective view of one individual well with a vertical mixing baffle.

FIG. 7b shows a perspective view of one individual well with an inner structure in form of a slope.

FIG. 7c shows a perspective view of one individual well with an inner structure in form of an asymmetric slope.

Figure 1:
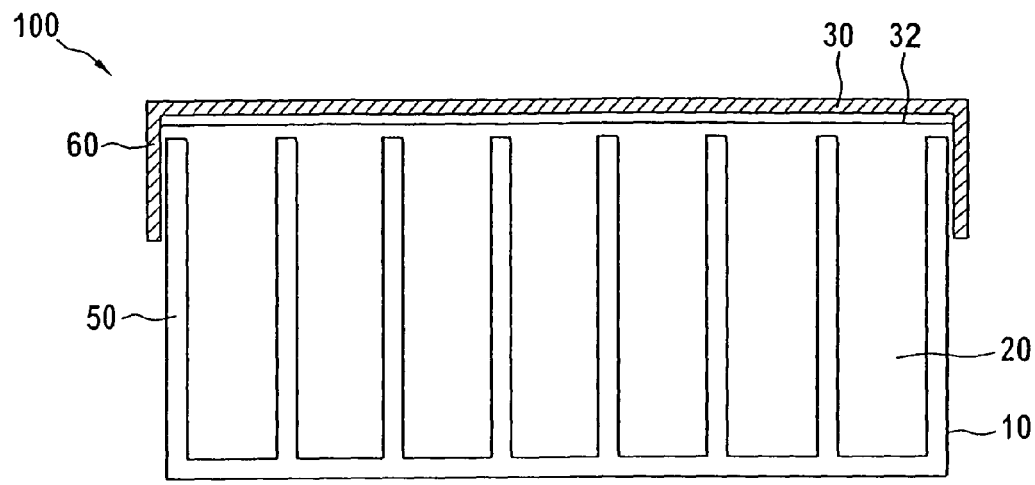
FIG. 1 is a cross-sectional view of the deepwell plate system according to the present invention.

Referring to FIG. 1 of the drawings, one embodiment of the deepwell plate system 100 according to the present invention is shown, consisting of deepwell plate 50 which comprises a plurality of wells 20 which are enclosed by frame 10 of deepwell plate 50. Each well 20 is open to the top for receiving, for example, liquid samples. Deepwell plate 50 comprising the plurality of wells 20 and frame 10 is essentially in form of a rectangle. Lid system 60 can be detachably fitted to deepwell plate 50 in order to seal the top openings of all wells 20 simultaneously in a liquid-tight fashion. Lid system 60 consists of at least outer cover 30 and inside filter membrane 32, generally having the same geometry as the principal surface of the deepwell plate 50.

Figure 2A:
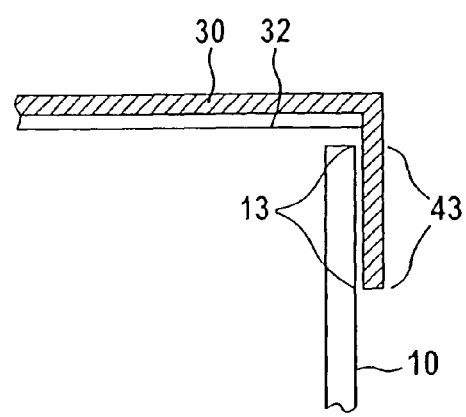
FIG. 2a shows a fragmentary cross-sectional view of the lid system of the deepwell plate system.

Referring to FIG. 2a, wherein lid system 60 of deepwell plate system 100 is shown in greater detail. Rim 43 of outer cover 30 mates with lid-matching upper portion 13 of frame 10. When lid system 60 is attached to deepwell plate 50, filter membrane 32 comes to lie on the upper surface of frame 10 and is preferably snugly compressed by the attachment of lid system 60 to deepwell plate 50.

Figure 2B:
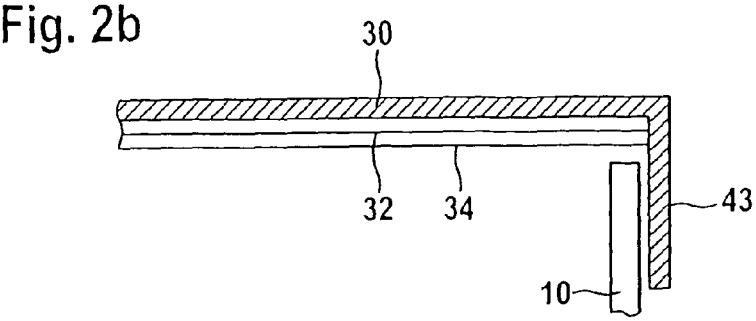
FIG. 2b shows a fragmentary cross-sectional view of an alternative embodiment of the lid system.

In another embodiment, and referring now to FIG. 2b of the drawings, lid system 60 comprises outer cover 30, filter membrane 32 and inner cover 34. Rim 43 of outer cover 30 is formed to overlap lid-matching upper portion 13 of frame 10. Filter membrane 32 and inner cover 34 preferably have the same geometry as the principle surface of the deepwell plate 50 facilitating their compression when lid system 60 is attached to deepwell plate 50. Hence, all openings of wells 20 are sealed by filter membrane 32 and inner cover 34 in a leak-tight fashion.

Preferably, outer cover 30 comprises small holes in a number according to the number of wells 20 of deepwell plate 50 which come to lie exactly above the center of the openings of wells 20. Filter membrane 32 preferably does not comprise any holes, but is permeable for gases to provide for the exchange of for example oxygen between the outside air and wells 20. Inner cover 34 comprises small holes in alignment with the center of the openings of wells 20 and is preferably made out of a resilient hydrophobic material. The deepwell plate system 100 thus achieves a hermetic sealing of wells 20 by virtue of compressing filter membrane 32 and inner cover 34 when lid system 60 is attached to deepwell plate 50 while still allowing gas exchange. This makes deepwell plate system 100 especially suitable for cell culture procedures.

Figure 3A:
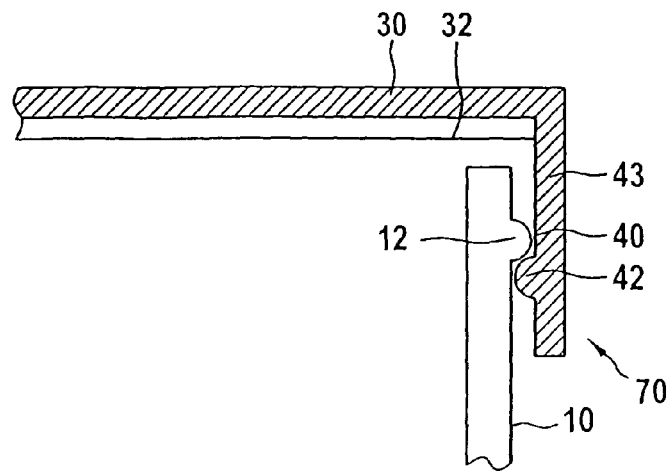
FIG. 3a is a fragmentary cross-sectional view of one embodiment of the lock element as a snap-fastening means.

Referring now to FIG. 3a, lock element 70 in one embodiment is a snap-fastening means. Rim 43 of outer cover 30 overlaps or matches the upper portion of frame 10. In this particular embodiment, plate-matching lower portion 40 of rim 43 of outer cover 30 comprises protrusion 42 extending inwardly, i.e. facing frame 10, preferably lid-matching upper portion 13. Lid-matching upper portion 13 of frame 10 on the other hand comprises protrusion 12 which extends outwardly, i.e. facing rim 43 of outer cover 30, preferably plate-matching lower portion 40. As at least outer cover 30 is made preferably of a resilient material, outer cover 30 comprising filter membrane 32 can simply be pushed downwards to close the deepwell plate 50 until protrusion 42 snaps or clicks over protrusion 12 thereby securing lid system 60 onto deepwell plate 50. To detach lid system 60 from deepwell plate 50, lid system 60 simply has to be pulled away from deepwell plate 50 using force until protrusion 42 of outer cover 30 disengages from protrusion 12 of frame 10 by snapping over protrusion 12.

Figure 3B:
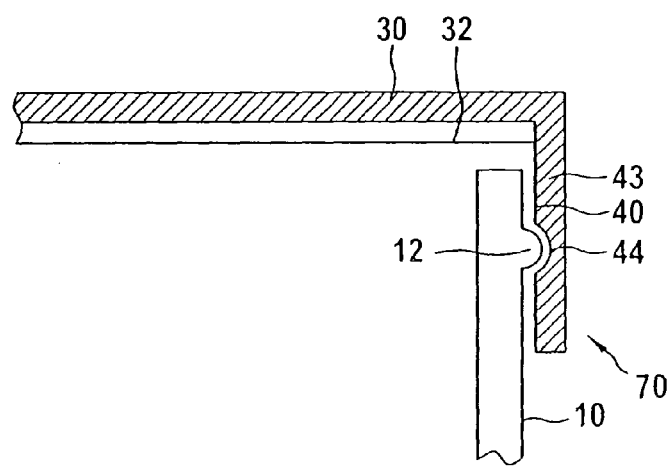
FIG. 3b shows a fragmentary cross-sectional view of another embodiment of the lock element as a snap-fastening means.

Another embodiment of lock element 70 as a snap-fastening means is shown in FIG. 3b. Here, plate-matching lower portion 40 of rim 43 of outer cover 30 features indentation or groove 44. To seal wells 20 of deepwell plate 50, lid system 60 can be pushed downwards until indentation 44 snaps over protrusion 12 of lid-matching upper portion 13 of frame 10.

Figure 3C:
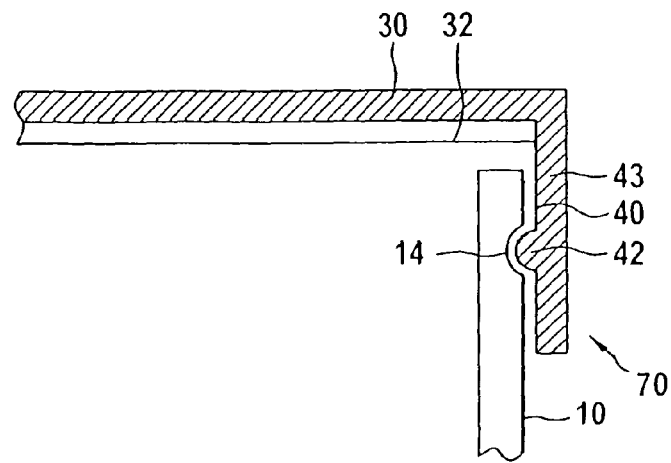
FIG. 3c is a fragmentary cross-sectional view of yet another embodiment of the lock element as a snap-fastening means.
Figure 8A:
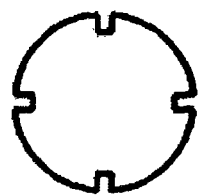
FIG. 8a shows the cross section of a well with four edged mixing baffles.
Figure 8B:
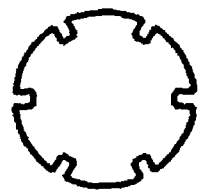
FIG. 8b shows the cross section of a well with six edged mixing baffles.
Figure 8C:
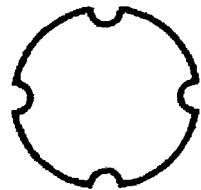
FIG. 8c shows the cross section of a well with four round mixing baffles.
Figure 8D:
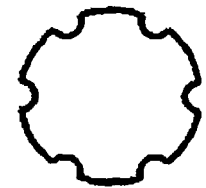
FIG. 8d shows the cross section of a well with six round mixing baffles.
Figure 8E:
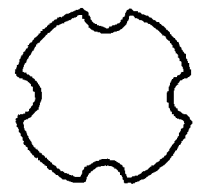
FIG. 8e shows the cross section of a well with four big round mixing baffles.
Figure 8F:
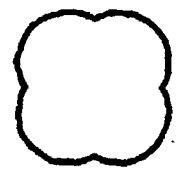
FIG. 8f shows the cross section of a well with a four-edged flower-shape.
Figure 8G:
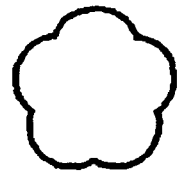
FIG. 8g shows the cross section of a well with a five-edged flower-shape.
Figure 8H:
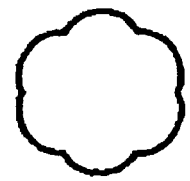
FIG. 8h shows the cross section of a well with a six-edged flower-shape.
Figure 8I:
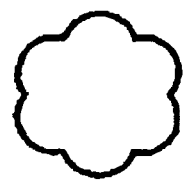
FIG. 8i shows the cross section of a well with a different six-edged flower-shape.
Figure 8J:
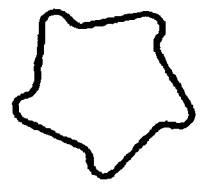
FIG. 8j shows the cross section of a well with a five-edged star-shape.
Figure 8K:
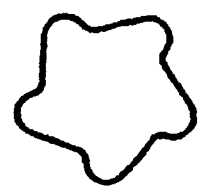
FIG. 8k shows the cross section of a well with a different five-edged star-shape.
Figure 8L:
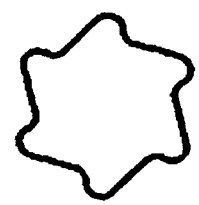
FIG. 8l shows the cross section of a well with a six-edged star-shape.
Figure 8M:
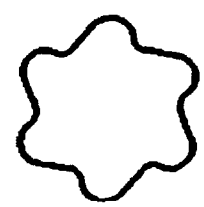
FIG. 8m shows the cross section of a well with a different six-edged star-shape.

Yet another embodiment of lock element 70 as a snap-fastening means is shown in FIG. 3c. In this embodiment plate-matching lower portion 40 of rim 43 of outer cover 30 features protrusion 42 extending inwardly, i.e. facing frame 10, preferably lid-matching upper portion 13 of frame 10. Lid-matching upper portion 13 of frame 10 on the other hand features indentation or groove 14. To close deepwell plate 50 with lid system 60, lid system 60 has simply to be pushed downwards until protrusion 42 snaps or clicks into indentation 14 of frame 10, thereby securing lid system 60 on deepwell plate 50.

All of the protrusion/indentation combinations shown in FIGS. 3a, b and c may be formed as pairs of at least two, which would then preferably be located on opposite sides of deepwell plate system 100, or at least one part of the protrusion/indentation combination is formed in a circumferential fashion.

Referring to FIG. 4a, another embodiment of lock element 70 is a clamp-fastening means. Here, rim 43 of outer cover 30 integrally provides clamp 46 which reaches to the side wall 47 of frame 10. Side wall 47 of frame 10 features notch or aperture 16. To secure lid system 60 onto deepwell plate 50, lid system 60 has to be pushed downwards until the hook-shaped end of clamp 46 engages with notch 16. For the purpose of detaching lid system 60 from deepwell plate 50, fastening clamp 46 can be pulled away from deepwell plate 50, so that it disengages from notch 16.

FIG. 4b shows a plan view of the deepwell plate system 100 closed by the clamp-fastening means of the lid system 60 described in detail in FIG. 4a.

Referring now to FIG. 5a, another embodiment of lock element 70 as a clamp-fastening means is shown in cross-sectional view. In this embodiment, side wall 47 of frame 10 of deepwell plate 50 integrally provides clamp 18. Clamp 18 is intended to be engaged with catch notch 48 provided by the rim 43 of outer cover 30. To close lid system 60, it is thus only necessary to push lid system 60 downwards until the hook-shaped end of clamp 18 clicks into catch notch 48. To detach lid system 60 from deepwell plate 50 fastening clamp 18 has to be pulled away from deepwell plate 50 so that the hook-shaped end of clamp 18 disengages from catch notch 48 and to relieve lid system 60 from deepwell plate 50.

FIG. 5b shows a plan view of deepwell plate system 100 closed by the clamp-fastening means of lid system 60 described in detail in FIG. 5a.

FIG. 6 shows perspective views of individual wells or deepwells 20 of deepwell plate 50 which can have round or square cross sections. It is to be appreciated that the bottom of the wells 20 can either be flat, U-shaped, V-shaped, in form of a frustum or any other suitable shape.

Referring now to FIG. 7a of the drawings, in one embodiment individual wells 20 of deepwell plate 50 comprise at least one inner structure, which can be vertical mixing baffle 26. Vertical mixing baffle 26 is formed by side wall 22 of deepwell 20. Mixing baffle 26 may be in the form of a straight fin, as shown, or may have a triangular or other shape. The base of mixing baffle 26 may extend across approximately one half of bottom 24 of well 20. Vertical mixing baffle 26 promotes in an advantageous manner mixing of the contents of well 20. It also increases the rate of oxygen transfer to the contents of the well 20.

Referring now to FIG. 7b, another embodiment of the inner structure of well 20 can be slope 28 of bottom 24. Slope 28 may extend across approximately one half, preferably the whole of bottom 24 of well 20 and may reach to approximately one half of the height of side wall 22 of well 20. This arrangement assists in moving suspended cells from the lower part of well 20 as the contents of the well are agitated.

Referring now to FIG. 7c, yet another embodiment of the inner structure of well 20 can be asymmetric slope 28. Asymmetric slope 28 is a projection or elevation of bottom 24 of well 20. The base of asymmetric slope 28 may extend across approximately one half, preferably the whole of bottom 24 of well 20 and reach to approximately one half of the height of side wall 22 of well 20.

FIGS. 8a to 8e depict different embodiments of vertical mixing baffles, in particular the cross section of a well with four edged mixing baffles (a), a well with six edged mixing baffles (b), a well with four round mixing baffles (c), a well with six round mixing baffles (d) and a well with four big round mixing baffles (e).

FIGS. 8f to 8i show another embodiment of different geometries of the cross sections of the wells, in particular the cross section of a well which is four-edged flower-shaped (f), the cross section of a well which is five-edged flower-shaped (g), the cross section of a well which is six-edged flower-shaped (h) and the cross section of a well which is of a different six-edged flower shape.

FIGS. 8j to 8m depict yet another embodiment of different well geometries, in particular the cross section of a well which is five-edged star-shaped (j), the cross section of a well which is of a different five-edged star shape (k), the cross section of a well which is six-edged star-shaped (l) and the cross section of a well which is of a different six-edged star shape.

The invention claimed is:

1. A deepwell plate system comprising
  a) a deepwell plate comprising a frame and 24 or 96 deepwells, wherein at least one well comprises at least one inner structure; and
  b) a lid system, comprising an inner cover, at least one filter membrane and an outer cover, wherein the outer cover covers simultaneously all of the openings of the deepwells and includes at least one integrated lock element as a first locking portion, wherein said first locking portion can be detachably fitted to at least one second locking portion located on the frame of the deepwell plate, and wherein the first locking portion of the outer cover is a snap-fastening means, wherein the snap-fastening means comprises as least a circumferential indentation as the first locking portion extending outwardly of a plate matching lower portion of the rim of the outer cover to be engaged with at least a complementary circumferential protrusion as to the second locking portion extending outwardly of a lid matching upper portion of the deepwell plate.

2. The plate system according to claim 1, wherein a cross section of at least one well is one of a circular shaped, flower-shaped or star-shaped.

3. The plate system according to claim 1, wherein the inner structure is a symmetric or asymmetric inner structure.

4. The plate system according to claim 1, wherein the inner structure is a projection or an elevation of the wall of the well.

5. The plate system according to claim 1, wherein the at least one inner structure of the wall of the well is a vertical mixing baffle.

6. The plate system according to claim 1, wherein the inner structure is a projection or an elevation of the bottom of the well.

7. The plate system according to claim 6, wherein the projection or elevation of the bottom of the well is a symmetric or asymmetric slope.

8. The plate system according to claim 1, wherein a horizontal cross section of at least one well is asymmetric.

9. The plate system according to claim 1, wherein the lid system is integrally composed of the outer cover and the at least one filter membrane.

10. The plate system according to claim 1, wherein the lid system is integrally composed of the outer cover, the at least one filter membrane and the inner cover.

11. A method for the cultivation of cells, wherein the cells are cultivated in a deepwell plate system according to claim 1.

* * * * *